United States Patent [19]
Phillips et al.

[11] Patent Number: 5,705,183
[45] Date of Patent: Jan. 6, 1998

[54] COTTON CANDY COATED MEDICATION AND A METHOD FOR MAKING AND ADMINISTERING THE SAME

[75] Inventors: Jon Phillips, South Beloit, Ill.; Troy W. Greenberg, Beloit, Wis.

[73] Assignee: Phillips Company, South Beloit, Ill.

[21] Appl. No.: 533,333

[22] Filed: Sep. 25, 1995

Related U.S. Application Data

[63] Continuation-in-part of Ser. No. 340,584, Nov. 16, 1994, abandoned.

[51] Int. Cl.⁶ .................................................. A61K 9/28
[52] U.S. Cl. .................. 424/439; 424/440; 424/464; 424/474; 424/465; 424/441; 424/479
[58] Field of Search .......................... 424/464, 439, 424/440, 441, 479, 465, 474

[56] References Cited

U.S. PATENT DOCUMENTS

| | | | |
|---|---|---|---|
| 207,013 | 8/1878 | Carter | 424/479 |
| 352,466 | 11/1886 | Huttemeyer | 424/440 |
| 2,757,124 | 7/1956 | Wolff | 167/82 |
| 3,798,054 | 3/1974 | Kawata et al. | 117/100 A |
| 3,930,043 | 12/1975 | Warning et al. | 426/515 |
| 4,139,589 | 2/1979 | Beringer et al. | 264/250 |
| 4,176,175 | 11/1979 | Maekawa et al. | 424/35 |
| 4,177,254 | 12/1979 | Khan et al. | 424/16 |
| 4,260,596 | 4/1981 | Mackles | 424/14 |
| 4,349,542 | 9/1982 | Staniforth | 424/153 |
| 4,421,738 | 12/1983 | Yamagiwa et al. | 424/35 |
| 4,511,552 | 4/1985 | Boesig et al. | 424/35 |
| 4,526,525 | 7/1985 | Oiso et al. | 425/9 |
| 4,545,989 | 10/1985 | Becker et al. | 424/154 |
| 4,749,575 | 6/1988 | Rotman | 424/441 |
| 4,832,956 | 5/1989 | Gergely et al. | 424/466 |
| 4,847,090 | 7/1989 | Della Posta | 424/440 |
| 4,855,326 | 8/1989 | Fuisz | 514/777 |
| 4,863,737 | 9/1989 | Stanley et al. | 424/440 |
| 4,873,085 | 10/1989 | Fuisz | 424/400 |
| 4,997,856 | 3/1991 | Fuisz | 514/777 |
| 5,011,532 | 4/1991 | Fuisz | 106/215 |
| 5,013,716 | 5/1991 | Cherukuri et al. | 514/23 |
| 5,028,632 | 7/1991 | Fuisz | 514/772 |
| 5,034,421 | 7/1991 | Fuisz | 514/772 |
| 5,073,374 | 12/1991 | McCarty | 424/435 |
| 5,095,035 | 3/1992 | Eby, III | 514/494 |
| 5,206,030 | 4/1993 | Wheatley et al. | 424/490 |
| 5,279,849 | 1/1994 | Fuisz et al. | 426/658 |
| 5,284,659 | 2/1994 | Cherukuri et al. | 424/441 |
| 5,288,498 | 2/1994 | Stanley et al. | 424/440 |
| 5,380,535 | 1/1995 | Geyer et al. | 424/484 |
| 5,391,378 | 2/1995 | Sanderson | 424/464 |
| 5,393,528 | 2/1995 | Staab | 424/436 |

*Primary Examiner*—Thurman K. Page
*Assistant Examiner*—James M. Spear
*Attorney, Agent, or Firm*—Hill, Steadman & Simpson

[57] ABSTRACT

A system and a method are provided to spray sugar in fibrous form and compress the same and subsequently add medication to form a dose appropriate for ingestion by a patient. Alternatively, the sprayed sugar in fibrous form may include the medication when sprayed. The sprayed sugar in fibrous form is advanced on a conveyor system and compressed into a stream. The compressed stream may have medication added thereto if not provided in the sprayed sugar in fibrous form. The stream may be combined with a second stream and then cut into individual, uniform doses of medication.

25 Claims, 3 Drawing Sheets

COTTON CANDY COATED MEDICATION AND A METHOD FOR MAKING AND ADMINISTERING THE SAME

This application is a continuation-in-part of U.S. Ser. No. 08/340,584 filed Nov. 16, 1994, now abandoned.

BACKGROUND OF THE INVENTION

The present invention is generally directed to medications and more specifically to a cotton candy-coated powdered medication and a method for making and administering the same.

Administering medications to a sick child has been and continues to be one of the most unpleasant tasks a parent must undertake. There are many factors that contribute to the difficulty in making a child take medication. For example, most children have a fear of doctors, drugs and medicine in general. In addition, many children have difficulty swallowing many medications in either liquid or tablet form because of a gag reflex caused by a mental phobia and taste aversion to many medications.

However, as proclaimed in the motion picture Mary Poppins, "Just a spoon full of sugar makes the medicine go down in the most delightful way." In an attempt to exploit this theory, several attempts have been made to alleviate the fears and anxiety for children taking medications by somehow sweetening the medication. A common example is to provide a type of fruit or candy flavoring to a liquid medication, such as flavored cough syrups.

Also, efforts to make medications for children fun to ingest have been attempted. For example, chewable vitamins having fruit flavors play to a child's love of candy. Also, many such medications are shaped in the form of a cartoon character, an animal, etc.

However, the known attempts to cater to children's likes do not provide a more effective way of actually administering the medication itself. For example, the fact that the medication tastes like candy does not aid in the physical ingestion of the medication.

Accordingly, a need has arisen for a highly-dissolvable candy-coated medication that facilitates physical ingestion of the medication by the patient. In addition, the related need for a method of making and administering such a medication also exists.

In addition, many of the same problems that occur with giving children medication are also found when treating a sick animal, such as a household pet like a dog. Many pets will not swallow their medication and cannot therefore be treated effectively. Thus, a similar need has arisen for a medication for animals.

SUMMARY OF THE INVENTION

As a result, the present invention provides a readily dissolvable cotton candy-coated medication and a method for making and administering the same.

In an embodiment of the present invention, a method is provided for making a coated medication. The method comprises the steps of: spraying a supply of a combination of sugar in fibrous form and medication to form a stream of the combination; compressing the stream to form a ribbon; and cutting the ribbon to form a plurality of individual units of the coated medication.

In an embodiment, a conveyor is provided which transports the stream and the ribbon to perform the compressing and the cutting.

In an embodiment, a compressing roll is provided which compresses the stream to form the ribbon.

In an embodiment, a cutting roll is provided to cut the ribbon to form the plurality of individual units.

In an embodiment, the stream is compressed to form a ribbon no greater that ½-inch in thickness.

In an embodiment, the plurality of individual units is uniformly cut.

In another embodiment of the present invention, a composition is provided which comprises a dose of medication and a sprayed layer of sugar in fibrous form incorporating the dose of the medication.

In an embodiment, the composition further comprises a masking agent formed with the dose of the medication. The dose of the medication and the sprayed layer of sugar in fibrous form are compressed to form a compressed combination.

In an embodiment, the dose of medication is added after the layer of sugar in fibrous form is sprayed.

In another embodiment of the present invention, a method is provided for administering medication to a patient. The method comprises the steps of: providing a dose of the medication and a sprayed layer of sugar in fibrous form incorporating the dose to form an ingestible tablet; and orally administering the tablet to a patient.

In another embodiment of the present invention, a method is provided for making a coated medication. The method comprises the steps of spraying a first supply of sugar in fibrous form onto a first transport means; spraying a second supply of sugar in fibrous form onto a second transport means; compressing the first supply on the first transport means to form a first stream; compressing the second supply on the second transport means to form a second stream; adding a dose of medication to the second stream; and combining the first stream and the second stream to form the medication.

In an embodiment, the method further comprises the step of cutting the medication into a plurality of uniformly sized doses.

In an embodiment, the first transport means and the second transport means are conveyors.

In an embodiment, a cutting roll is provided for cutting the medication after combining the first stream and the second stream.

In another embodiment of the present invention, a system is provided for making a coated medication. The system comprises a first spraying means capable of spraying a first supply of sugar in fibrous form and a second spraying means capable of spraying a second supply of sugar in fibrous form. Means is provided for adding medication to one of the first supply and the second supply and further for compressing the first supply and the second supply to form a compressed stream of the medication. The means for compressing compresses each of the first supply and the second supply before adding the medication.

In an embodiment, cutting means is constructed and arranged to cut the compressed stream of the coated medication. The cutting means may be a roller.

It is, therefore, an advantage of the present invention to provide a coated dose of a medication.

Another advantage of the present invention is to provide a dose of a medication that is quickly dissolvable and, hence, easily ingested by a patient. Moreover, an advantage of the present invention is to provide a medication that is easily ingested by a patient having physical and/or mental difficulties which impair his or her ability to take medication, i.e., stroke victims, mentally retarded persons, etc.

A further advantage of the present invention is to provide a method for making a coated medication in a simple manner.

Yet another advantage of the present invention is to provide a medication that is quickly dissolvable and easily administered to a patient.

A still further advantage of the present invention is to provide a method of easily and effectively administering a quickly dissolvable medication to a patient having mental and/or physical impediments to taking medications, i.e., small children, stroke victims, mentally retarded persons, etc.

And, another advantage of the present invention is to provide a system and a method for combining any type of medication to a stream of compressed sugar in fibrous form.

Moreover, an advantage of the present invention is to provide a system and a method that is capable of combining any medication due to use of sprayed sugar in fibrous form that is subsequently compressed before medication is added.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a dose of a powdered medication and a layer of cotton candy surrounding the dose of the powdered medication. The cotton candy-coated dose of the powdered medication is made by a method having the steps of providing a supply of cotton candy, pulling the supply of cotton candy into a compressed ribbon, cutting the ribbon into a plurality of pieces, providing a dose of powdered medication, arranging the dose of powdered medication between at least two of the pieces of cotton candy to form a sandwich and compressing the sandwich to thereby coat the dose of powdered medication with the pieces of cotton candy.

Figure 1:
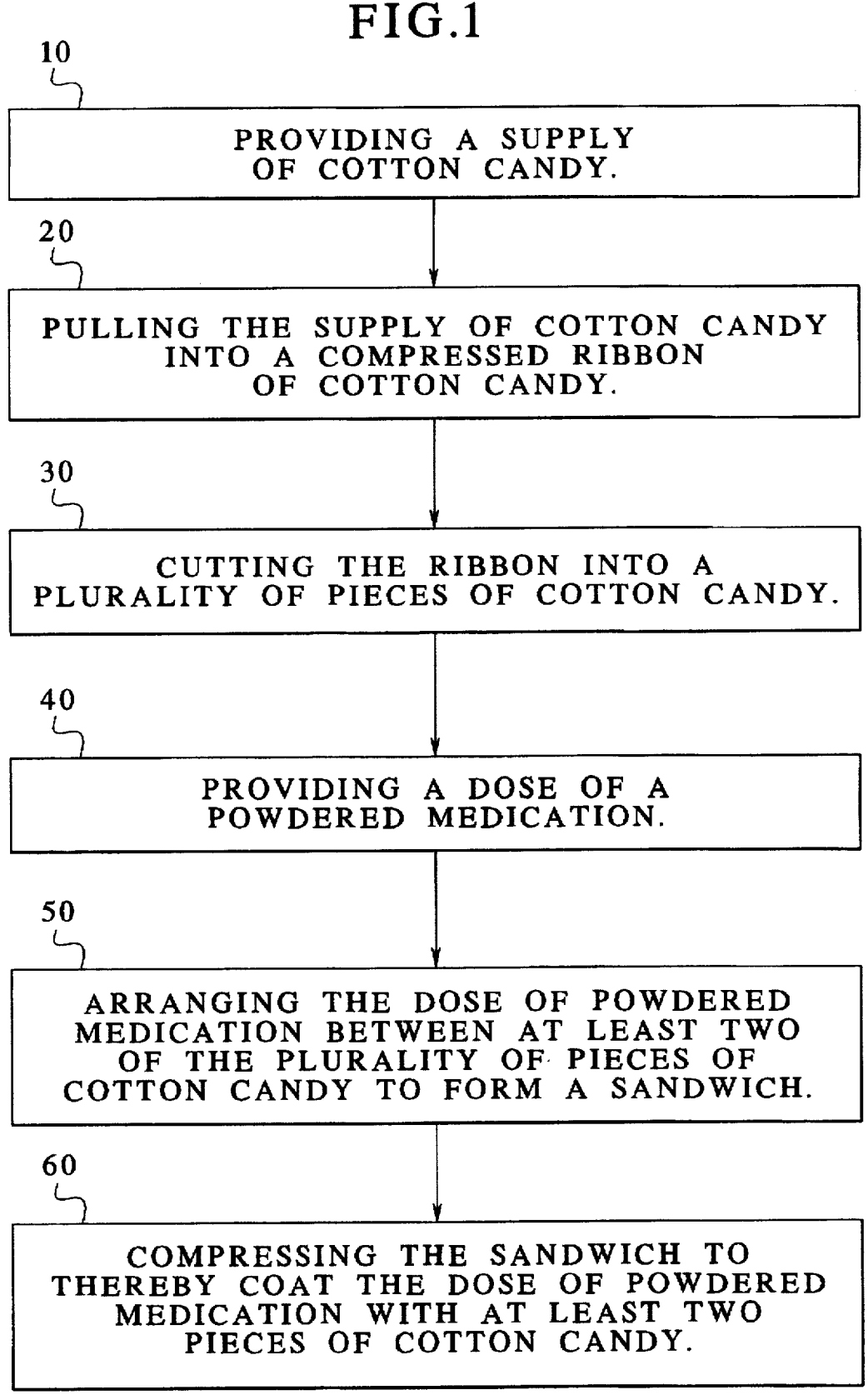
FIG. 1 illustrates a flowchart of an embodiment of the method of the present invention.

Now referring to the embodiments of the present invention as illustrated in the figures, FIG. 1 shows a flowchart of the method steps enumerated above of the present invention. A description of the method follows.

Taking each step in turn, the first step 10 is to provide a supply of cotton candy. This may be done in a standard manner. However, a customized cotton candy machine could be used. For example, "Tracy spinners" may be used to produce the cotton candy. The cotton candy used in the present invention consists essentially of sugar, food coloring and a powdered dye. Of course, other known compositions may be used to produce the present invention. The next step 20 involves pulling the supply of cotton candy into a compressed ribbon of cotton candy. The supply of cotton candy is pulled from the cotton candy machine by a conveyor belt to form the ribbon. In an embodiment, the ribbon of cotton candy is approximately one-quarter inch thick and one inch wide.

Then, the ribbon is cut into a plurality of pieces as shown at 30 in FIG. 1. In an embodiment, the pieces are approximately one inch-square by one-quarter inch thick.

The plurality of pieces are subsequently compressed into individual, uniformly-shaped pieces as shown at 40 in FIG. 1. The uniformly-shaped pieces provide a standardized shape that is easier to work with in the method steps that follow. In an embodiment, the uniformly-shaped pieces can be wafers approximately one-eighth of an inch thick. However, various sizes and shapes are possible and within the scope of the present invention.

The method then provides, as shown at 50 in FIG. 1, a dose of a powdered medication. The dose is preferably an amount that would be appropriate for a child. The powdered medication may be a cold remedy, headache medicine, pain reliever, etc. Additionally, animal medications could be provided in appropriate doses.

Subsequently, at the step designated as 60 in FIG. 1, the dose of the powdered medication is arranged between at least two of the plurality of pieces of cotton candy to thereby form a sandwich (see FIG. 2). In a preferred embodiment, the size of the powdered medication is relatively smaller than the size of the cotton candy pieces so that the cotton candy can completely surround and coat the medication.

The final step 70 of the method of the present invention involves compressing the sandwich (formed of at least two pieces of cotton candy with a dose of powdered medication between them) to thereby surround and coat the dose of powdered medication with the pieces of cotton candy.

In a preferred embodiment, the compressed sandwich has the approximate dimensions of one-quarter inch thick by less than one inch square.

Figure 2:
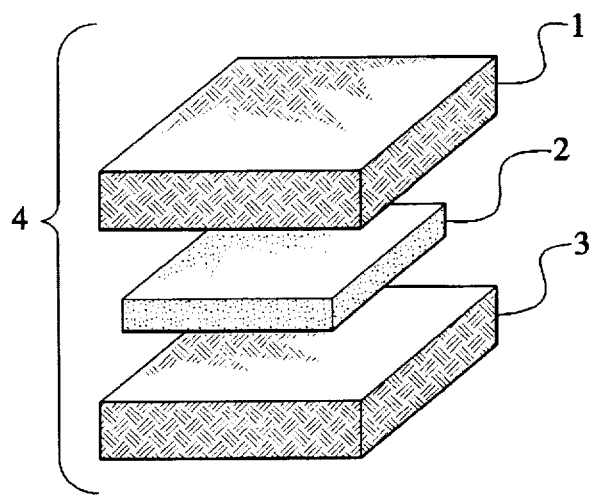
FIG. 2 illustrates an exploded view of an embodiment of a composition manufactured in accordance with the method of the present invention.

FIG. 2 illustrates an exploded view of the components of the cotton candy-coated medication composition of the present invention. Specifically, FIG. 2 illustrates a top piece of cotton candy 1 and a bottom piece of cotton candy 2 having the approximate dimensions of one-quarter inch thick by one inch square. The pieces of cotton candy 1, 2 result from the performance of the first three steps of the method of the present invention.

Also, FIG. 2 illustrates a dose of a powdered medication 3 that is located between the two pieces of cotton candy 1, 2. The three pieces 1, 2, 3 form a sandwich 4 having the powdered medication 3 (shown exaggerated in size) surrounded by the top piece of cotton candy 1 and the bottom piece of cotton candy 2. The powdered medication 3 is substantially smaller than the two pieces of cotton candy 1, 2. In this manner, it is assured that the pieces of cotton candy 1, 2 fully surround the medication 3 so that complete coating is provided. Thus, a sweetness barrier between the patient's taste buds and the medication is provided to aid in the pleasant administration of the medication 3. Thus, prior to the final compression step of the method of the invention, the sandwich 4 has an approximate thickness of one-half inch, wherein the powdered medication is approximately 1/64 of an inch thick.

Figure 3:
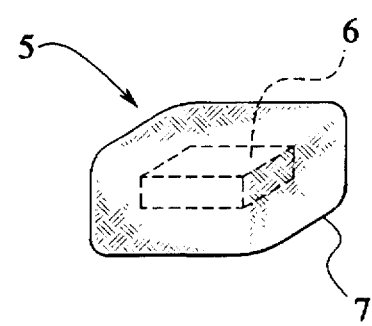
FIG. 3 illustrates a perspective view of an embodiment of the composition of the present invention in final manufactured form.

FIG. 3 illustrates an embodiment of the cotton candy-coated medication of the present invention in final form after the final method step of compressing the sandwich 4. As illustrated, the sandwich 4 of FIG. 2 is compressed on all sides to form a capsule 5 having a compressed powder medication core 6 and a cotton candy coating 7 completely surrounding the core 6. After compression, the cotton candy-coated medication capsule 5 has a thickness of approximately 1/8 of an inch.

FIG. 3 also illustrates the composition of the present invention. Specifically, the composition includes a dose of a powdered medication and a layer of cotton candy surrounding the dose of powdered medication. In an embodiment, the dose is preferably an amount that is appropriate for a child. In addition, the dose may be an amount that is appropriate for an animal, such as a pet dog.

Figure 4:
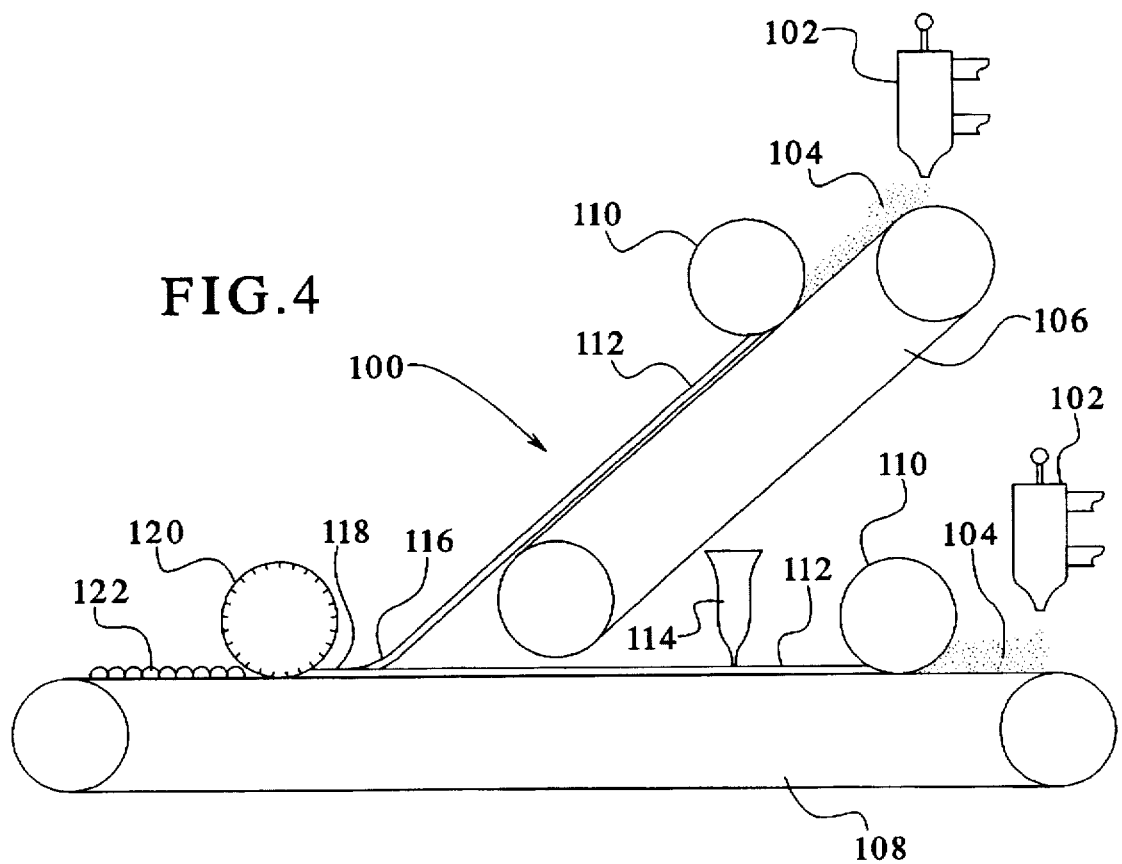
FIG. 4 illustrates a schematic diagram of the components necessary for carrying out the method of the invention illustrated with reference to the flowchart in FIG. 5.
Figure 5:
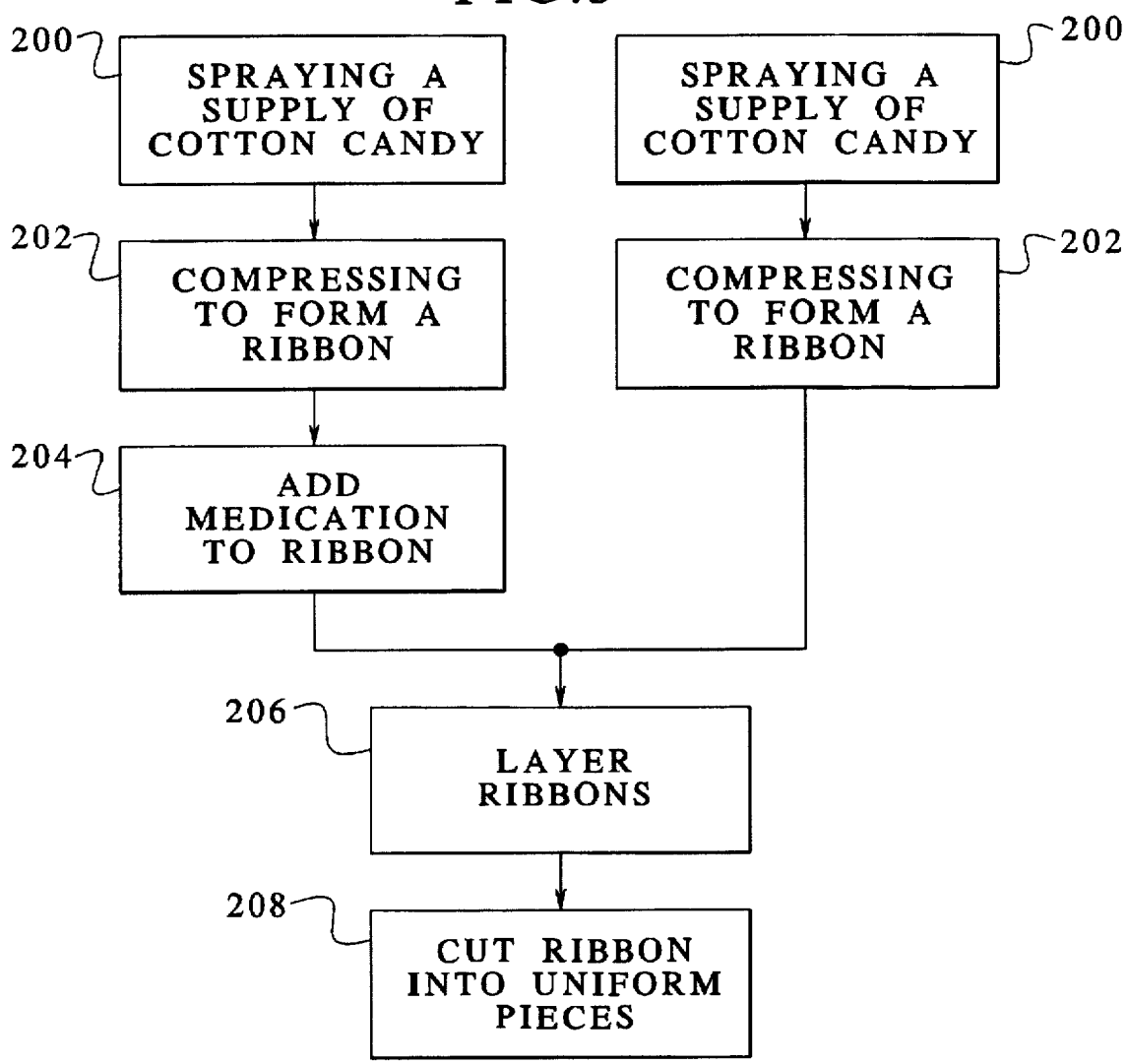
FIG. 5 illustrates a flowchart of another embodiment of the method of the present invention.
Figure 6:
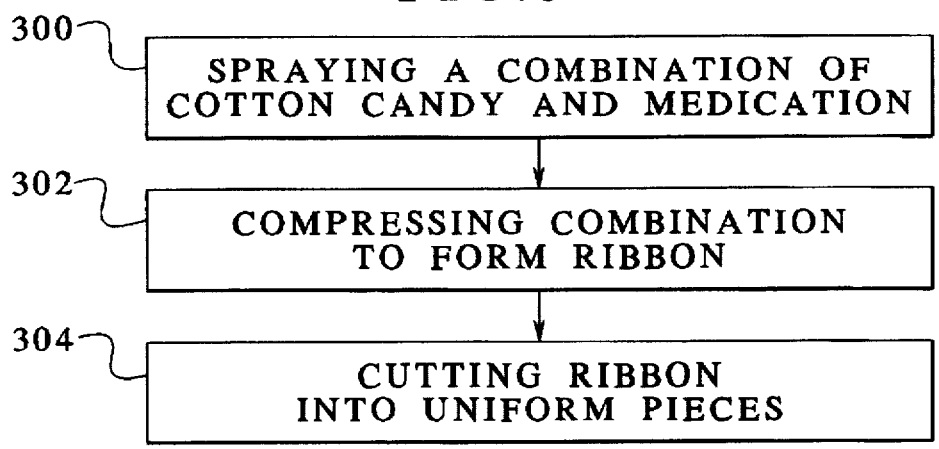
FIG. 6 illustrates a flowchart of another embodiment of the method of the present invention.

Referring now to FIGS. 4–6, alternate embodiments of the present invention are illustrated for manufacturing a coated medication. A first embodiment of a system 100 for making the coated medication is illustrated in FIG. 4 with reference to the steps set forth in FIG. 5. In the embodiments illustrated, a highly efficient spraying system and method are employed to form sugar in fibrous form rather than the more traditional spinning method commonly known.

To this end, the system 100 includes a pair of spray nozzles 102. The spray nozzles 102 discharge a supply of sugar in fibrous form 104 therefrom. The sugar in fibrous form 104 is discharged from the spray nozzles 102 in a manner shown and described in U.S. Pat. No. 3,723,134 to Chivers, the disclosure of which is incorporated herein in its entirety by reference. The sugar in fibrous form 104 is fed onto one of two conveyors 106 and 108. Preferably, the belt of the conveyor system is manufactured from a food grade nylon material. The belts of the conveyors 106, 108 are driven and controlled by motors (not shown) as is conventionally known in the art.

Compression rolls 110 are provided downstream on each of the conveyors 106, 108. The compression rolls 110 compress the sugar in fibrous form 104 into a compressed ribbon 112. Downstream from the compression roll 110 of the conveyor 108 is a medication spotter 114. The medication spotter 114 is controlled in a conventional manner to add a dose of medication to the ribbon 112 on the conveyor 108. Since the compressed ribbon 112 has substantially cooled in temperature from the temperature of the sprayed sugar in fibrous form originally discharged from the spray nozzle 102, any type of medication may be added to the compressed ribbon without regard to the effects of temperature on the medication.

The conveyors 106, 108 are constructed and arranged such that the ribbons 112 from each of the conveyors 106, 108 converge to meet at a point 116 such that the ribbon 112 on the conveyor 106 layers on top of the ribbon 112 on the conveyor 108. The layered ribbon 118 is advanced on the conveyor belt 108 under a cutting roll 120. The cutting roll 120 cuts the layered ribbon 118 into a plurality of individual pieces 122 for packaging or the like as required.

Preferably, the ribbon 112 is compressed to a thickness of 0.100 inches and has a width of approximately six inches. Of course, any sized ribbon 112 may be formed by those skilled in the art and is dependent on the amount of sprayed sugar in fibrous form 104 supplied from the spray nozzles 102 and the size of the compression roll 110 on the conveyors 106, 108.

The method performed by the system 100 of FIG. 4 is laid out in the flowchart of FIG. 5. As shown, a supply of sugar in fibrous form is sprayed at the step 200 from each of a pair of nozzles. Then, the sprayed sugar in fibrous form is compressed at step 202 to form a ribbon. One of the ribbons has medication added thereto as shown at step 202. The ribbons are layered at step 206 and then cut into a plurality of individual pieces as illustrated at step 208.

An alternate method of forming the coated medication is illustrated by the flowchart of FIG. 6. As shown, the sugar in fibrous form is first sprayed. However, before spraying the same, medication is mixed with the sugar such that, from the nozzles, a combination of sugar in fibrous form and medication is sprayed. The combination is compressed as illustrated at step 302 to form a ribbon. Following compression into the ribbon, the ribbon is cut into a plurality of individual pieces as shown at step 304. This method, however, may limit the types of medication that may be used due to the temperature required to conduct the spraying of the cotton candy. Typically, compressed air above 366° F. is used with sugar vacuumed through a hose from a venturi.

In addition to the composition of the coated medication and the method of making the same, the present invention further provides a method of administering the coated medication to a patient. The patient can be either human or animal, i.e. a pet dog. The composition is also advantageous for use with patients having mental and/or physical impairments to taking medications, i.e., stroke victims, comatose patients, small children, mentally retarded persons, etc.

To this end, the present invention provides a method for administering the medication to a patient having the step of orally administering a dose of a powdered medication and a layer of cotton candy surrounding the dose of powdered medication to a patient. The present invention has the advantage of being extremely dissolvable in the mouth of the patient. This advantage results from the fact that the cotton candy has the property of being very quickly dissolved in the mouth of a patient. In addition, the medication being in powdered form increases the dissolving rate. This is especially advantageous when the patient has mental and/or physical impairments to taking medications, i.e., stroke victims, small children, mentally retarded persons, comatose patients, etc.

Also, the cotton candy has a pleasing, sweet sugary flavor for the patient to enjoy which masks the flavor of the medication. An additional masking agent may be added to further mask the taste of the medication. In the present invention, the masking is especially effective due to the fact that the cotton candy coating comes into contact with the patient's taste buds before the medication does. The above advantages provide for easier administration of the medication to an unwilling patient, such as a child or a pet dog.

While the above description discloses cotton candy, known variations of common cotton candy (i.e., spun sugar) will be apparent to those skilled in the art and are considered within the scope of the present invention. Also, the multitude of medications can include antihistamines, acetaminophen, aspirin, etc. Those skilled in the art will recognize the innumerable medications that can be prepared in the present method and are deemed to be within the present disclosure.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A method of making a coated medication, the method comprising the steps of:
   spraying a supply of a combination of sugar in fibrous form and medication to form a stream of the combination without spinning of the supply;
   compressing the stream to form a ribbon; and
   cutting the ribbon to form a plurality of individual units of the coated medication.

2. The method of claim 1 further comprising:
   providing a conveyor; and
   transporting the stream and the ribbon on the conveyor to perform the compressing and the cutting.

3. The method of claim 1 wherein a compressing roll compresses the stream to form the ribbon.

4. The method of claim 1 wherein a cutting roll cuts the ribbon to form the plurality of individual units.

5. The method of claim 1 wherein the stream is compressed to form a ribbon no greater than ½-inch in thickness.

6. The method of claim 1 wherein the plurality of individual units are uniformly cut.

7. A composition comprising:
   a dose of medication;
   a supply of sugar capable of being sprayed in fibrous form and forming a sprayed layer that incorporates the dose of the medication wherein the layer is formed without spinning and further wherein the dose of the medication and the sprayed layer of sugar in fibrous form are compressed to form a compressed combination.

8. The composition of claim 7 further comprising:
   a taste masking agent formed with the dose of the medication.

9. A system for making a coated medication, the system comprising:
   a first spraying means capable of spraying a first supply of sugar in fibrous form;
   a second spraying means capable of spraying a second supply of sugar in fibrous form;
   means for adding medication to one of the first supply and the second supply; and
   means for compressing the first supply and the second supply to form a compressed stream of the coated medication; and
   cutting means constructed and arranged to cut the compressed stream of the coated medication.

10. The composition of claim 7 wherein the dose of medication is added after the layer of sugar in fibrous form is sprayed.

11. A method of administering medication to a patient, the method comprising the steps of:
    providing a dose of the medication and a sprayed layer of sugar in fibrous form incorporating the dose to form an ingestible tablet; and
    orally administering the tablet to a patient.

12. The method of claim 11 wherein the patient is human.

13. A method of making a coated medication, the method comprising the steps of:
    spraying, without spinning, a first supply of sugar in fibrous form onto a first transport means;
    spraying, without spinning, a second supply of sugar in fibrous form onto a second transport means;
    compressing the first supply on the first transport means to form a first stream;
    compressing the second supply on the second transport means to form a second stream;
    adding a dose of medication to the second stream; and
    combining the first stream and the second stream to form the coated medication.

14. The method of claim 13 further comprising the step of:
    cutting the medication into a plurality of uniformly sized doses.

15. The method of claim 13 wherein the first transport means and the second transport means are conveyors.

16. The method of claim 13 further comprising the steps of:
    providing a cutting roll; and
    cutting the medication with the cutting roll after combining the first stream and the second stream.

17. A system for making a coated medication, the system comprising:
    a first spraying means capable of spraying a first supply of sugar in fibrous form without spinning the first supply;
    a second spraying means capable of spraying a second supply of sugar in fibrous form without spinning the second supply; means for adding medication to one of the first supply and the second supply; and
    means for compressing the first supply and the second supply to form a compressed stream of the coated medication.

18. The system of claim 17 wherein the means for compressing compresses each of the first supply and the second supply before adding the medication.

19. The system of claim 17 further comprising:
    cutting means constructed and arranged to cut the compressed stream of the coated medication.

20. The system of claim 19 wherein cutting means is a roller.

21. A method of making a coated medication, the method comprising the steps of:
    spraying a first supply of sugar in fibrous form onto a first transport means;
    spraying a second supply of sugar in fibrous form onto a second transport means;
    compressing the first supply on the first transport means to form a first stream;
    compressing the second supply on the second transport means to form a second stream;
    adding a dose of medication to the second stream;
    combining the first stream and the second stream to form the coated medication; and
    cutting the medication into a plurality of uniformly sized doses.

22. A method of making a coated medication, the method comprising the steps of:
    spraying a first supply of sugar in fibrous form onto a first transport means;
    spraying a second supply of sugar in fibrous form onto a second transport means;
    compressing the first supply on the first transport means to form a first stream;
    compressing the second supply on the second transport means to form a second stream;
    adding a dose of medication to the second stream; and
    combining the first stream and the second stream to form the coated medication wherein the first transport means and the second transport means are conveyors.

23. A method of making a coated medication, the method comprising the steps of:
- spraying a first supply of sugar in fibrous form onto a first transport means;
- spraying a second supply of sugar in fibrous form onto a second transport means;
- compressing the first supply on the first transport means to form a first stream;
- compressing the second supply on the second transport means to form a second stream;
- adding a dose of medication to the second stream;
- combining the first stream and the second stream to form the coated medication;
- providing a cutting roll; and
- cutting the medication with the cutting roll after combining the first stream and the second stream.

24. A system for making a coated medication, the system comprising:
- a first spraying means capable of spraying a first supply of sugar in fibrous form;
- a second spraying means capable of spraying a second supply of sugar in fibrous form;
- means for adding medication to one of the first supply and the second supply; and
- means for compressing the first supply and the second supply to form a compressed stream of the coated medication wherein the means for compressing compresses each of the first supply and the second supply before adding the medication.

25. The system of claim 9 wherein the cutting means is a roller.

* * * * *